United States Patent [19]

Lee et al.

[11] 4,149,982

[45] Apr. 17, 1979

[54] EXTREME PRESSURE ADDITIVES FOR LUBRICANTS

[75] Inventors: Donald A. Lee, Cleveland; John A. Boslett, Cleveland Heights, both of Ohio

[73] Assignee: The Elco Corporation, Cleveland, Ohio

[21] Appl. No.: 236,325

[22] Filed: Mar. 20, 1972

[51] Int. Cl.² .................. C10M 1/38; C10M 3/32; C10M 5/28; C10M 7/36
[52] U.S. Cl. .................................................. 252/48.6
[58] Field of Search ............................... 252/45, 48.6

[56] References Cited

U.S. PATENT DOCUMENTS

| | | | |
|---|---|---|---|
| 1,974,299 | 9/1934 | Churchill | 252/48.6 |
| 2,167,439 | 7/1939 | Kaufman | 252/48.6 |
| 2,179,061 | 11/1939 | Smith | 252/48.6 |
| 3,238,130 | 3/1966 | Matson | 252/45 X |
| 3,455,896 | 7/1969 | Herder et al. | 252/48.6 X |
| 3,664,955 | 5/1972 | Panzer | 252/45 |
| 3,825,495 | 7/1974 | Newingham et al. | 252/48.6 |

*Primary Examiner*—Delbert E. Gantz
*Assistant Examiner*—Irving Vaughn
*Attorney, Agent, or Firm*—Paul & Paul

[57] ABSTRACT

Extreme pressure additives are provided which are used in lubricant compositions. The extreme pressure additives of this invention are prepared by sulfurizing a mixture comprised of (a) 50-85% by weight of an ester of a higher fatty acid and glycerol, or a mono-lower-aliphatic ester of fatty acid, or mixtures thereof and (b) 50-15% by weight of a mono-alpha-unsaturated olefin having about 15-20 carbon atoms. The extreme pressure additives of this invention are especially useful in improving the high pressure characteristics of greases, gear oils, way lubricants and the like.

4 Claims, 1 Drawing Figure

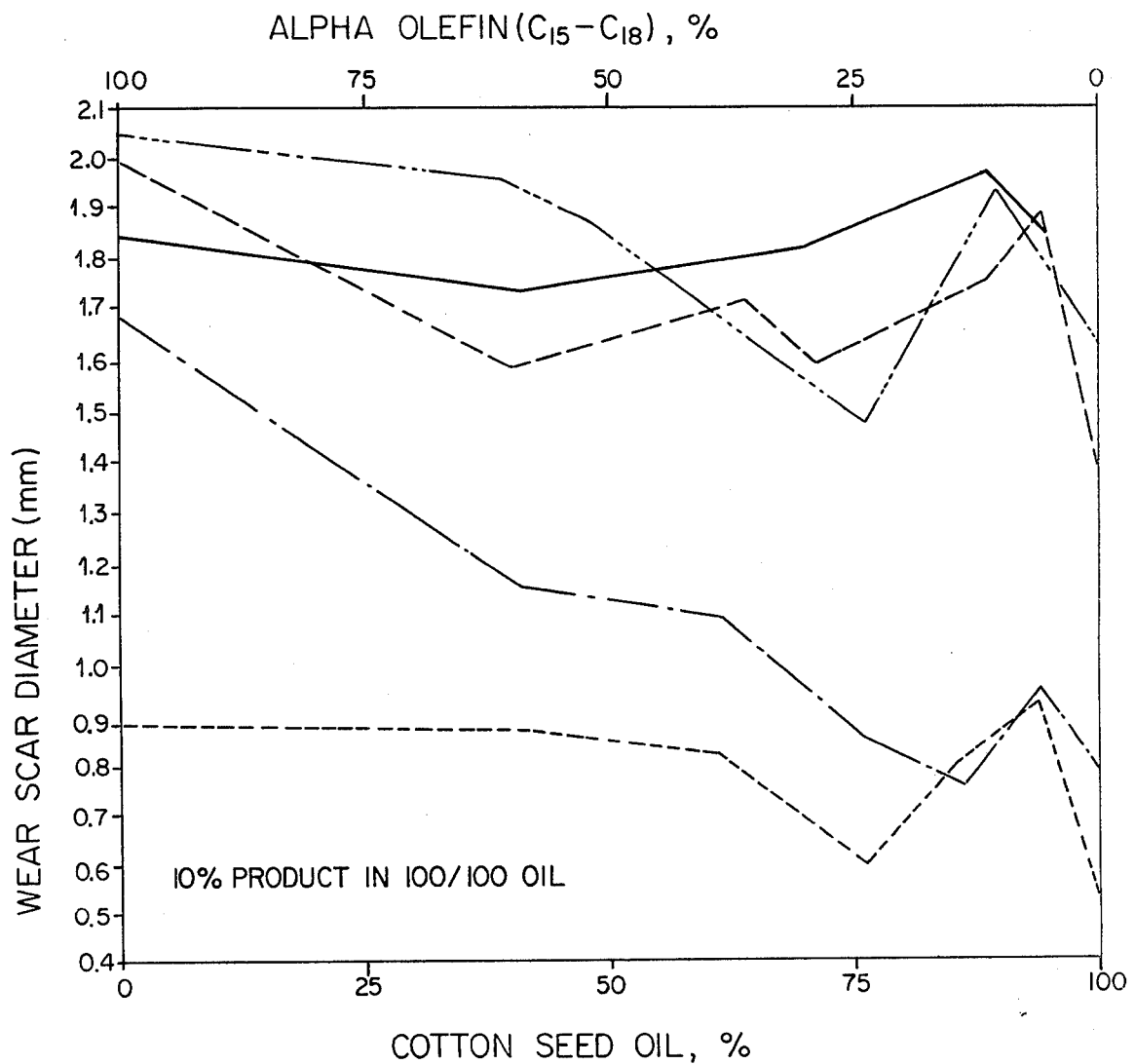

EXTREME PRESSURE ADDITIVES FOR LUBRICANTS

BACKGROUND OF THE INVENTION

1. Field of the Invention

This invention is concerned with novel extreme pressure additives and with lubricant compositions containing said additives.

2. Background of the Invention

Lubricants are widely used to reduce the friction between surfaces of moving parts and thereby reduce the wear and prevent damage to the parts. Most of the lubricants are comprised principally of a base stock which is generally a relatively high molecular weight hydrocarbon. In applications where the amount of pressure applied to the moving part is quite high, lubricants which are comprised of only hydrocarbon base stock tend to fail and the parts in contact are damaged.

It is well known to add materials to increase the high pressure performance of lubricants. These materials are generally referred to as extreme pressure additives. The most commonly used extreme pressure additives are sulfurized unsaturated fatty materials such as sulfurized sperm whale oil. It is believed that in the sulfurization process the sulfur adds to the double bonds to form monosulfides and disulfides.

One of the problems encountered in the manufacture of sulfurized extreme pressure additives is that raw materials used in certain of these additives vary considerably in price and availability. A typical example of such a raw material is sperm whale oil. The number of sperm whales harvested each year is decreasing. Accordingly, with the decrease in the supply, the cost has markedly increased. Furthermore, since there is a possibility that sperm whales may become extinct due to overkill, the sperm whale has been classified as an endangered species. To prevent continued hunting of the sperm whale it has been suggested that the importation of sperm whale oil be prohibited and thereby thus eliminate the market.

With the exception of sperm whale oil other common fatty materials have not proven to be completely satisfactory for use in extreme pressure additives. While sperm whale oil is a special case with regard to availability, other oils and fats used in extreme pressure lubricants can vary considerably in price, availability and quality from time to time. A poor crop of corn, for example, can markedly increase the price of corn oil because of the resulting limited supplies.

One of the principal problems with most extreme pressure additives is one of compatability with the lubricant base stock. Many fatty materials when sulfurized do not form clear solutions with the lubricant base stock. The resulting mixtures are hazy to definitely cloudy and even, in certain cases, the additives will precipitate from the mixtures. Lubricants which are sold for use in high pressure applications must be clear, in order to be commercially acceptable. The resason for this is obvious in that the lubricants will be subject to extreme conditions in use and accordingly it is felt that a hazy mixture under normal conditions would be more likely to break down under extreme pressure conditions.

A further problem is that certain starting fatty materials are highly reactive in the sulfurizing process. As a result, there is believed to be an excessive amount of sulfur cross-linking which adversely effects both the solubility and extreme pressure characteristics of the additives formed from these materials.

The most important factor to be considered in the selection of any extreme pressure additive is the effect it will have on preventing damage to the surfaces which are in sliding contact. The effect of extreme pressure on a lubricant can be seen by the fact that the SAE load-carrying capacity of a typical naphthenic base oil without an extreme pressure additive is only about 25 pounds. However, the addition of 4.5% of sulfurized sperm whale oil increases the load carrying capacity from 25 pounds to 312 pounds, as reported in Table 1 of the paper "Influence of Chemical Structure in Sulfurized Fats on Antiwear Behavior" by A. Dorinson, American Society of Lubrication Engineers Preprint 70LC-8.

SUMMARY OF THE INVENTION

An object of this invention is to provide a new class of extreme pressure additives which are soluble in lubricant base stocks, impart extreme pressure capability to the lubricant base stock, and which can be made from a variety of starting materials.

Other objects and advantages of this invention will become more apparent from a continued reading of the specification and claims.

The objects of this invention have been achieved by providing a class of extreme pressure additives which are the sulfurized reaction product of (a) 50–85% by weight of an ester of a higher fatty acid and glycerol, or a monolower aliphatic ester of a fatty acid, or a mixture thereof and (b) 50–15% by weight of an alpha-mono-unsaturated olefin having 15–20 carbon atoms.

BRIEF DESCRIPTION OF THE DRAWING

The FIGURE is a graph of the scar diameters (m.m.) obtained using various sulfurized mixtures of cottonseed oil and $C_{15}$–$C_{18}$ α olefin in 100/100 oil under extreme pressure conditions in the Barry test, as shown in Table 1.

DESCRIPTION OF THE PREFERRED EMBODIMENTS

The extreme pressure additives of this invention are sulfurized mixtures of (a) an ester of a higher fatty acid and glycerol, or a mono-lower-aliphatic ester of a fatty acid, or mixtures thereof and (b) a mono-alpha-unsaturated olefin.

The esters of the higher fatty acids and glycerol are most preferably obtained from natural sources because of the ready availability and relatively low cost. These esters can be represented by the general formula:

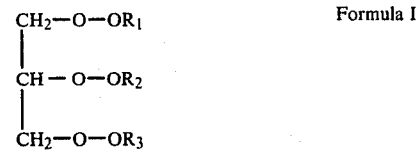

Formula I $$\begin{array}{c} CH_2-O-OR_1 \\ | \\ CH-O-OR_2 \\ | \\ CH_2-O-OR_3 \end{array}$$

wherein $R_1$, $R_2$ and $R_3$ may be the same or different, each being obtained from a higher fatty acid.

In addition to an ester of higher fatty acids and glycerol it is also possible to use mono-lower (1–8 carbon atoms) aliphatic esters of fatty acids. It is preferable to use mixtures of esters of fatty acids and glycerol. Mixtures of various esters of fatty acids and glycerol are found in naturally occuring fats and oils. It likewise is possible to use mixtures of esters of fatty acids and glycerol and mono-lower-aliphatic esters of higher fatty acids.

An important factor in selection of the esters of the fatty acid is the amount of unsaturation. The reason for this is that it is believed that the sulfur which is added during sulfurization reacts with the double bonds to form sulfides. It should be noted that the oils and fats when sulfurized are effective as extreme pressure lubricants, while in the unsulfurized state they are not effective as extreme pressure additives.

It has been found that the amount of unsaturation present in the starting esters is to some extent critical. If there is too low a degree of unsaturation the esters will not react with a sufficient amount of sulfur to produce a satisfactory product. On the other hand, if the degree of unsaturation is excessively high over-sulfurization can occur with cross-linking between the double bonds of the acid residues. The most satisfactory products are obtained with esters of fatty acids and glycerol, mono-lower-aliphatic esters of high fatty acids and mixtures, which have a degree of unsaturation such that the iodine number is between about 40 and 200.

Typical naturally occuring oil and fats which can advantageously be used to prepare the extreme pressure additives of this invention are lard, castor oil, olive oil, peanut oil, rape oil, corn oil, cottonseed oil, soybean oil, sunflower oil, linseed oil, tung oil, safflower oil, lard oil, sperm whale oil, whale oil and fish oil. The most preferable of the naturally occuring oils and fats are cottonseed oil and lard oil because of the excellent results obtained using these materials and their relatively constant supply and cost stability.

All of the fats and oils noted above are comprised principally of esters of fatty acids and glycerol. The fatty acids components can be myristic, palmitic, stearic, palmitoleic, oleic, and linoleic acid residues. The fats and oils may also contain minor amounts of other acids and other compounds in addition to the esters.

The monoesters are obtained in the conventional manner, for example, by reacting a lower (1–8 carbon atoms) aliphatic alcohol with higher fatty acids such as one of those noted above. It is most preferably to use a straight chain saturated alcohol having the hydroxyl group on the terminal carbon atom.

At this point it should be noted that the oil and fats noted above, if simply sulfurized, do not in general have the properties desired in an extreme pressure additive. The principal shortcoming of the materials is that they lack solubility in base lubricant stocks and form cloudy mixtures or precipitate from the base lubricant stocks.

It has been found quite surprising that if the above described fats and oils or monoesters are blended with certain alpha-unsaturated olefins and the mixture sulfurized that both the solubility of the final product and the extreme pressure properties are substantially improved with the co-sulfurized mixture thus formed. The alpha-unsaturated olefins which are used in the preparation of the extreme pressure additives of this invention should have about 15–20 carbon atoms and most preferably 15–18 carbon atoms. The olefins should be mono-unsaturated with the unsaturation being at the alpha carbon atom. Most preferably the olefins should be straight chain olefins but it is also possible to use branched chain olefins. The commercially available mono-alpha-olefins often contain minor amounts of diolefins and paraffins. If the content of the alpha-mono-unsaturated olefin in the mixture is above 80–90% no difficulties are encountered.

The sulfur is added in various amounts depending upon the desired end use of the extreme pressure additive and to some extent upon the specification provided by the customer concerning sulfur content. In general, 8–16% by weight of sulfur is added with optimum results being obtained with about 10.5–11% by weight of sulfur, based on the total weight of the mixture of the esters and alpha olefin. When it is desired to produce a product containing a relatively large amount of sulfur, for example, up to 16%, it is preferable to use a fat or oil having a relatively high iodine number, for example, cottonseed oil.

In order to obtain an effective extreme pressure additive it is important that a mixture of the (1) (a) esters of the higher fatty acids and glycerol, (b) monoester of a higher fatty acid or (c) mixtures thereof and (2) the alpha olefin be blended in certain critical proportions. Sulfurized oils such as cottonseed oil are insoluble in typical lubricant base stock such as 100/100 oil and accordingly are unsuitable, but the extreme pressure characteristics imparted to the lubricant base stock are, however, satisfactory.

On the other hand, sulfurized alpha olefins have excellent solubility in lubricant base stock, but are poor in the relative degree of increase in extreme pressure characteristics imparted to the lubricant base stock.

As a result of the tests with pure sulfurized cottonseed oil and pure sulfurized alpha olefins it was expected that by blending the cottonseed oil and alpha olefin together and then sulfurizing the mixture that there would be an averaging of the properties. It was believed that the addition of the alpha olefin would increase the solubility in lubricant base stock but likewise would reduce the extreme pressure properties. The addition of the cottonseed oil was expected to proportionately increase the extreme pressure properties but decrease the solubility in the lubricant base stock.

The prediction was found accurate for most of the various combinations of sulfurized cottonseed oil and alpha olefin. Turning to the FIGURE, which will be described in greater detail in the examples, the scar diameter of various combinations of sulfurized cottonseed oil and alpha olefin oil were evaluated at several loadings and speeds. The lower the reported scar diameter the better is the extreme pressure properties of the additive.

As noted above, the sulfurized alpha olefin was poor in extreme pressure properties. However, as the amount of cottonseed oil was increased the extreme pressure properties increased as shown in the graph. The wear scar diameter reached a low point when the ratio was within the range of 50–85% by weight cottonseed oil and 50–15% by weight of alpha olefin. More specifically, it should be noted that the optimum results using a wide variety of loading was generally best when the cottonseed oil comprised 70–82% of the composition and the alpha olefin was present in an amount of 30–18%.

What was highly surprising was that the extreme pressure characteristics rapidly deteriorated when the concentration of cottonseed oil was increased to about 90%. As the amount of cottonseed oil was further increased toward 100% the high pressure properties again increased but the blends were cloudy and accordingly unacceptable.

The other oils tested including corn oil, lard oil, and the like showed the same critical property ranges as that shown for cottonseed oil. The sulfurized products obtained using 50-85% of the ester of the fat or oil and 50-15% of alpha olefin are unique in being excellent extreme pressure additives and also in being compatible and soluble in the commonly employed lubricant base stock. The sulfurized mixture comprised of 70-82% by weight of the ester of the fatty acids and 20-18% by weight of alpha olefins are especially suitable.

The amount of the extreme pressure additive used in a given lubricant formulation can vary from a few percent to about 15%. For most applications the amount used is between 4-10% depending upon the end use. In gear oil for use in selective light duty application 4% is generally quite sufficient. However, way lubricants for heavy equipment generally will contain large amounts of 10% or more because of the relatively high pressure applied.

The lubricant base stock can be selected from a large class of compounds. Most often the base is a high molecular weight hydrocarbon. The extreme pressure additives of this invention can be used with oils like 100/100 oil, greases and so fourth.

The following examples are given by way of further illustration and are not intended to limit the scope of the invention beyond that of the subjoined claims. All parts and percentages are by weight not volume unless otherwise noted.

EXAMPLE 1

Mixtures containing various percentages of cottonseed oil and alpha olefin were sulfurized. The cottonseed oil employed had an iodine number of 194. The alpha olefin employed was a mixture of $C_{15}$-$C_{18}$ alpha olefins, comprised of 91% by weight of alpha olefins with 8% by weight of diolefins and 1% by weight of paraffins. Both the cottonseed oil and the alpha olefin were clear and free of sediment.

The mixtures were sulfurized with 11% by weight of the total weight of the mixture using flowers of sulfur. The process condition included initial blending of the starting material together. The reaction mixtures were then heated to 320-360° F. for 6 hours with continuous stirring. The resulting mixtures were cooled to 100-200° F. and air was blown through the mixtures for an additional 6 hours.

The amount of cottonseed oil, alpha olefin and sulfur employed in each mixture is shown in Table 1. Each mixture was evaluated for viscosity and solubility. The extreme pressure properties of the sulfurized mixtures were evaluated using Mean Hertz and Weld tests in accordance with ASTM D 2783-69T. A wear test was conducted using the Shell Four Ball Test. These tests did not disclose the significant difference between the additives which was observed in actual field tests. A further test was run in accordance with the test procedures reported by Barry and Binkleman in the paper entitled "A Wear Tester For The Evaluation Of Gear Oil", published in the January 1971 issue of "Lubrication Engineering" which was presented at the 25th ASLE Annual Meeting, May 4-8, 1970. This test, referred to in the chart as the Barry test, clearly demonstrated the criticallity of the combinations of oils for the extreme pressure additive. The results obtained are shown in the table and graphed on the FIGURE.

TABLE I

| Sample No. | % alpha olefin | % cotton seed oil | Viscosity at 210° F. S.U.S. | 10% in solvent extracted neutral 100/100 oil | 10% mid-continental solvent extracted base stock SAE 90 | Mean Hertz (KG) ASTM |
|---|---|---|---|---|---|---|
| 1 | 0 | 100 | 847 | Hazy with precipitate | Hazy with precipitate | 35.2 |
| 2 | 22.8 | 77.2 | 272 | Clear | Clear | 37.5 |
| 3 | 59.0 | 59.0 | 89.0 | Clear | Clear | 36.1 |
| 4 | 63.8 | 36.2 | 183 | Clear | Clear | 36.0 |
| 5 | 87.5 | 12.5 | 403 | Clear | Hazy | 34.5 |
| 6 | 94.9 | 5.1 | 522 | Clear | Hazy with | 37.9 |
| 7 | 100 | 0 | 50.2 | Clear | Clear | 29.8 |

| Sample No. | Seizure (KG) ASTM | Weld (KG) 4 BallShell | Wear 20 KG 130° F., 1000 RPM 1 HR 4 Ball Shell |
|---|---|---|---|
| 1 | 71 | 316 | 0.560 |
| 2 | 71 | 316 | 0.539 |
| 3 | 71 | 282 | 0.587 |
| 4 | 71 | 282 | 0.574 |
| 5 | 71 | 282 | 0.553 |
| 6 | 79 | 316 | 0.560 |
| 7 | 56 | 224 | 0.595 |

| Sample No. | BARRY TEST | | | | | |
|---|---|---|---|---|---|---|
| | 1600 CPM/20 LB | 2100 CPM/11 LB | 2600 CPM/2 LB | Reverse Spring | | |
| | | | | 1600/2 LB | 2100/11 LB | 2600/20 LB |
| 1 | 1.63 | 1.39 | 0.88 | 0.51 | 1.41 | 1.61 |
| 2 | 1.82 | 1.59 | 0.84 | 0.59 | 1.13 | 1.47 |
| 3 | 1.74 | 1.59 | 1.15 | 0.86 | 1.78 | 1.95 |
| 4 | 1.80 | 1.72 | 1.09 | 0.81 | 1.87 | 2.02 |
| 5 | 1.97 | 1.75 | 0.76 | 0.80 | 1.53 | 1.93 |
| 6 | 1.84 | 1.88 | 0.93 | 0.92 | 1.57 | 1.80 |
| 7 | 1.85 | 2.00 | 1.69 | 0.88 | 1.88 | 2.12 |

EXAMPLE 2

A mixture of 80% by weight of corn oil having an iodine number of 190 and 20% by weight of the alpha olefin used in Example 1 were sulfurized with 12% by weight of sulfur as described in Example 1. The product was added in an amount of 10% by weight to 100/100 oil. It was completely soluble and formed a clear solution. The high pressure characteristics were similar to the properties of the material prepared in Example 1.

EXAMPLE 3

Example 1 was repeated except that a lard oil having an iodine number about 55 was used in place of the cottonseed oil and the amount of sulfur was reduced to 8%. The product was soluble and exhibited extreme pressure properties though it was not considered to be as satisfactory in actual use as the product of Example 1.

EXAMPLE 4

Example 1 was repeated using coconut fat having an iodine number of 8-10 in place of the cottonseed oil. When the sulfur was added a considerable amount precipitated from the reaction product. In addition, the product that was obtained after removal of the unreacted sulfur had poor solubility and poor extreme pressure properties. It should be noted that materials such as coconut fat having low iodine numbers are not included in the scope of this invention.

EXAMPLE 5

The product produced in Example 1 was evaluated against a sulfurized sperm oil derivative having the same sulfur content. It should be noted that the sulfurized sperm oil product did not contain an alpha olefin and heretofore was the standard by which other extreme pressure additives were evaluated. In extensive laboratory tests and field trials it was found that the sulfurized cottonseed oil-alpha olefin derivative was at least as good, if not superior, to the sperm oil derivatives in performance. It should be noted that the use of cottonseed oil and alpha olefin in place of sperm whale oil relieves the pressure on the supply of sperm whale oil and provides a considerably more reliable source of raw material.

We claim:

1. A method of imparting to a lubricant composition a substantial improvement in the extreme pressure characteristics of said lubricant composition without substantially impairing the degree of transparency of said lubricant composition, comprising the step of combining with a lubricant composition at least 4% by weight of a lubricant additive consisting essentially of a sulfurized mixture of: (a) about 50-85% by weight of a first member consisting of a mixture of an ester of a higher fatty acid and glycerol, and a synthetic mono-lower-aliphatic ester having 1-8 carbon atoms of a higher fatty acid, said first member having an iodine number from about 40-200 and (b) about 50-15% by weight of a second member selected from the group consisting of (1) a mono-alpha-unsaturated olefin having about 15-20 carbon atoms, and (2) mixtures of such olefins, said mixture being sulfurized with 8-16% by weight of sulfur based on the total weight of said first and second members.

2. The lubricant composition consisting essentially of a gear oil and an effective amount of a lubricant additive consisting essentially of a sulfurized mixture of: (a) about 50-85% by weight of a first member consisting of a mixture of an ester of a higher fatty acid and glycerol, and a synthetic mono-lower-aliphatic ester having 1-8 carbon atoms of a higher fatty acid, said first member having an iodine number from about 40-200 and (b) about 50-15% by weight of a second member selected from the group consisting of (1) a mono-alpha-unsaturated olefin having about 15-20 carbon atoms, and (2) mixtures of such olefins, said mixture being sulfurized with 8-16% by weight of sulfur based on the total weight of said first and second members, said effective amount being an amount sufficient to substantially increase the extreme pressure performance of said gear oil without substantially impairing the degree of transparency of said gear oil.

3. The lubricant composition of claim 2 wherein said lubricant additive is present in an amount of at least 4% by weight of the lubricant composition.

4. The lubricant composition consisting essentially of a way lube and an effective amount of a lubricant additive containing essentially of a sulfurized mixture of: (a) about 50-85% by weight of a first member consisting of a mixture of an ester of a higher fatty acid and glycerol, and a synthetic mono-lower-aliphatic ester having 1-8 carbon atoms of a higher fatty acid, said first member having an iodine number from about 40-200 and (b) about 50-15% by weight of a second member selected from the group consisting of (1) a mono-alpha-unsaturated olefin having about 15-20 carbon atoms, and (2) mixtures of such olefins, said mixture being sulfurized with 8-16% by weight of sulfur based on the total weight of said first and second members, said effective amount being an amount sufficient to substantially increase the extreme pressure performance of said way lube.

* * * * *

UNITED STATES PATENT OFFICE
CERTIFICATE OF CORRECTION

Patent No. 4,149,982     Dated April 17, 1979

Inventor(s) Donald A. Lee, John A. Boslett

It is certified that error appears in the above-identified patent and that said Letters Patent are hereby corrected as shown below:

Claim 4, line 3, "containing" should read --consisting--

Signed and Sealed this

Twenty-third Day of October 1979

[SEAL]

Attest:

RUTH C. MASON
Attesting Officer

LUTRELLE F. PARKER
Acting Commissioner of Patents and Trademarks